US011110231B2

(12) United States Patent
Cartiere et al.

(10) Patent No.: US 11,110,231 B2
(45) Date of Patent: Sep. 7, 2021

(54) SAFETY AND FILLING SYSTEM FOR RETRACTABLE NEEDLES SYRINGES

(71) Applicant: P&P Patents and Technologies S.R.L., Rome (IT)

(72) Inventors: Carmelo Raffaele Cartiere, Battipaglia (IT); Giuseppe Profiti, Rome (IT); Rosario Valles, Bellizzi (IT); Pantaleo Mauro, Lecce (IT)

(73) Assignee: P&P Patents and Technologies S.R.L., Rome (IT)

( * ) Notice: Subject to any disclaimer, the term of this patent is extended or adjusted under 35 U.S.C. 154(b) by 0 days.

(21) Appl. No.: 17/051,186

(22) PCT Filed: May 16, 2019

(86) PCT No.: PCT/IT2019/050103
§ 371 (c)(1),
(2) Date: Oct. 28, 2020

(87) PCT Pub. No.: WO2019/224850
PCT Pub. Date: Nov. 28, 2019

(65) Prior Publication Data
US 2021/0085894 A1 Mar. 25, 2021

(30) Foreign Application Priority Data
May 22, 2018 (IT) .................. 102018000005604

(51) Int. Cl.
*A61M 5/50* (2006.01)
*A61M 5/315* (2006.01)
*A61M 5/31* (2006.01)

(52) U.S. Cl.
CPC .......... *A61M 5/502* (2013.01); *A61M 5/3135* (2013.01); *A61M 5/31511* (2013.01);
(Continued)

(58) Field of Classification Search
CPC .......... A61M 5/31501; A61M 5/31513; A61M 5/31505; A61M 5/502; A61M 5/3135;
(Continued)

(56) References Cited

U.S. PATENT DOCUMENTS 4,820,272 A * 4/1989 Palmer ................ A61M 5/5013
604/110
4,826,483 A * 5/1989 Molnar, IV ......... A61M 5/5013
604/110
(Continued)

FOREIGN PATENT DOCUMENTS

FR 2707503 A1 1/1995

OTHER PUBLICATIONS

International search report in application No. PCT/IT2019/050103, dated Jul. 29, 2019.
(Continued)

*Primary Examiner* — Nathan R Price
*Assistant Examiner* — Justin L Zamory
(74) *Attorney, Agent, or Firm* — Oppedahl Patent Law Firm LLC

(57) ABSTRACT

The present invention relates to an innovative system which definitively prevents the re-use of syringes with retractable needles, allowing at the same time to fill the tank by means of a mechanical system installed inside the piston. The operation that aims at preventing the re-use of the device takes place through a mechanical system that prevents the return of the piston towards the initial position of aspiration and restricts, therefore, its action in a single direction and prevents the return of the plunger to the initial position of injection and therefore restricts its action in a single direction. Moreover a rotating mechanical transition system prevents the repositioning of the piston in the previously used position. The filling of the container, instead, takes place through the use of a system via a flexible cannula placed inside the piston.

7 Claims, 3 Drawing Sheets

(52) U.S. Cl.
CPC ............... *A61M 2005/3128* (2013.01); *A61M 2005/5026* (2013.01)

(58) Field of Classification Search
CPC ............ A61M 5/31511; A61M 5/5066; A61M 2005/3128; A61M 2005/5026; A61M 2005/5033; A61M 2005/5073; A61M 2005/31523
See application file for complete search history.

(56) References Cited

U.S. PATENT DOCUMENTS

| | | | | |
|---|---|---|---|---|
| 4,915,695 | A * | 4/1990 | Koobs | A61M 5/315 222/137 |
| 4,921,486 | A * | 5/1990 | DeChellis | A61M 5/315 604/110 |
| 4,978,339 | A * | 12/1990 | Labouze | A61M 5/5013 604/110 |
| 5,250,030 | A * | 10/1993 | Corsich | A61M 5/5013 604/110 |
| 5,328,476 | A * | 7/1994 | Bidwell | A61M 5/5013 604/110 |
| 6,494,863 | B1 | 12/2002 | Shaw | |
| 2003/0114797 | A1* | 6/2003 | Vaillancourt | B29C 48/16 604/171 |
| 2012/0289899 | A1 | 11/2012 | Wu | |

OTHER PUBLICATIONS

Written Opinion in application No. PCT/IT2019/050103, dated Jul. 29, 2019.

* cited by examiner

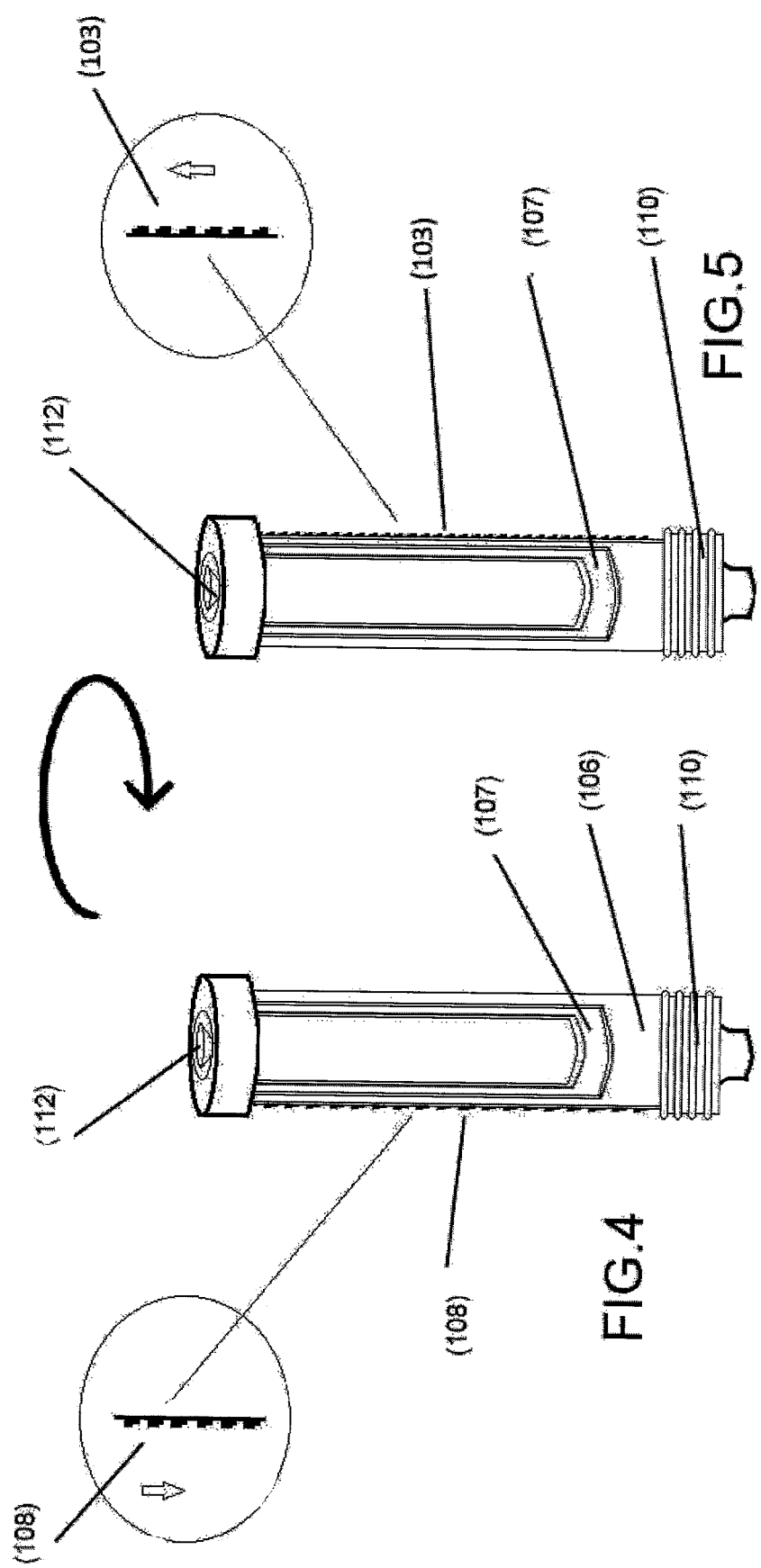

SAFETY AND FILLING SYSTEM FOR RETRACTABLE NEEDLES SYRINGES

The present invention relates to an innovative system which definitively prevents the re-use of syringes with retractable needles, allowing at the same time to fill the tank by means of a mechanical system installed inside the piston.

Healthcare professionals, such as nurses, doctors, veterinary surgeons, dentists, as well as waste disposal workers, are subjected daily to the risk of accidental punctures from inoculation systems previously used for medical therapies or else, which have come into direct contact with biological fluids of living beings potentially carrying transmissible infectious diseases.

Accidental punctures caused by previously used inoculation systems represent the most frequent and dangerous mode of exposure to communicable diseases. In fact, there are over forty transmissible pathogens, through blood or biological fluids, following an accidental puncture. Among them: the human immunodeficiency virus (HIV), the hepatitis B virus (HBV) and the hepatitis C virus (HCV). The problems connected to the management of biological risk by public and private health systems entail very high and unsustainable costs both from the economic and psychological point of view by those people who suffer the physical injury of an accidental puncture.

But the containers for the introduction or extraction by non-natural way of medicinal substances must not only guarantee the safety from the risk of accidental punctures, but also the impossibility of reuse.

In fact, it is a general custom, especially in countries with a lower economic profile, to re-use containers for the reintroduction of pharmacological substances after the administration of vaccines or other medicines.

On the market there are different types of retractable needle syringes, some also subject to special patent, whose security systems can be bypassed, as often happens, by not completing the piston stroke inside the container, thus allowing the reuse of the device.

It should also be highlighted the use cases of containers of medicinal substances, in vaccination campaigns and for the administration of antithrombotic drugs, where the containers themselves are supplied to health facilities pre-filled with the drugs.

The filling of the drugs is carried out by the pharmaceutical companies to which the containers are supplied completely disassembled. Thereafter, the pharmaceutical companies assemble them at different stages following the filling with the drug.

This approach, by significantly increasing operators' manipulation, increases the risk of contamination in the numerous preparation phases.

Although attempts have been made to limit these problems in all ways, some of which are also present in a number of patents, including EP2445554B1, U.S. Pat. No. 3,998,224A, 4,252,118A, 4,391,273A, 4,687,467A, 5,062,833A, 5,205,825A as well as the RU2236873 and WO1998001174A1 patents, they can in no way completely inhibit the syringes from reuse as well as cannot offer a simple and effective way of filling the syringe without using the needle.

The aforementioned criticalities are overcome by the present invention which allows the introduction and extraction of substances from the human or animal body preventing the re-use of the device by a practically inviolably means and also specifies a separate way for filling the container with ready to use medicines.

The operation that aims at preventing the re-use of the device takes place through a mechanical system that:

a) once the action of aspiration of the medicinal substance in the device has begun, it prevents the return of the piston towards the initial position of aspiration and restricts, therefore, its action in a single direction;

b) once the injection of the medicinal substance has begun in the device, it prevents the return of the plunger to the initial position of injection and therefore restricts its action in a single direction; as well, a rotating mechanical transition system, placed between the suction and injection operations consisting of a block that guides the piston, prevents the re-positioning of the piston in the previously used position.

The filling of the container, instead, takes place through the use of a system via a flexible cannula placed inside the piston, through which the desired substance is conveyed so that the same is poured inside the container, and thereafter be ready to be injected.

The present invention will now be described, for illustrative purposes, according to a preferred embodiment thereof, not to be understood in any limiting way, with particular reference to the figures and to the attached drawings, bearing in mind that all the embodiments used, without prejudice to their functionality, may vary in size, numbers and shape without this limiting the present invention:

FIG. 4 shows the "U" shaped system of channels on the piston and the rack system;

FIG. 5 shows another view of the "U" shaped system of channels on the piston and of the rack system;

Figures 1, 2, 3:
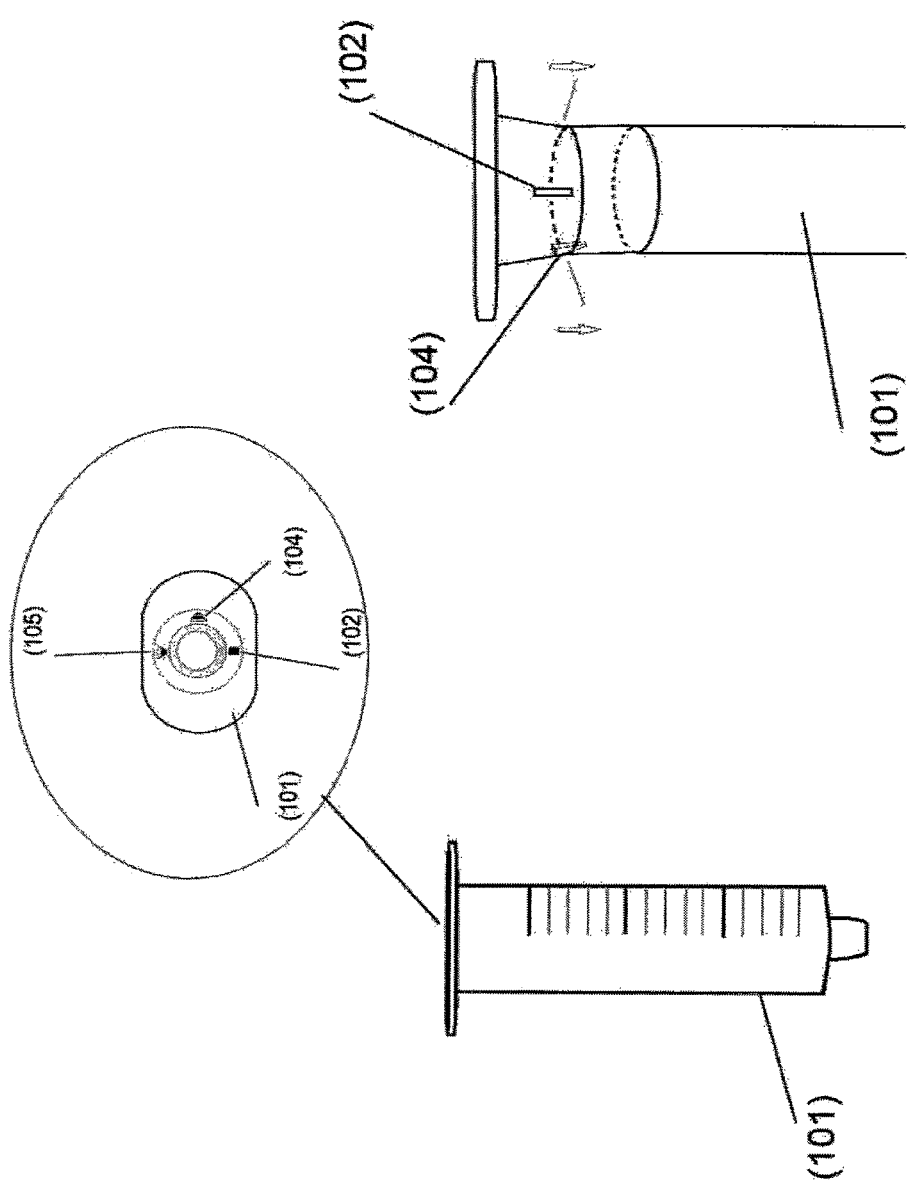
FIG. 1 shows the container, with emphasis in the box, as a view from above, of the fins and the ratchet.
FIG. 2 shows a section of the container with a fin and the ratchet.
FIG. 3 shows a further view of the container with a fin and the ratchet.
Figure 9:
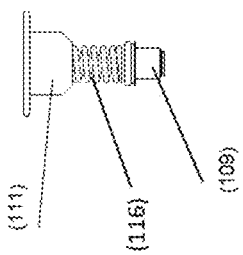
FIG. 9 shows the details of the mechanical system housed inside the piston when it is compressed.
Figure 8:
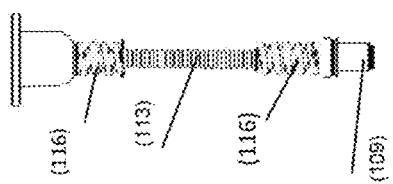
FIG. 8 shows the details of the mechanical system housed inside the piston.
Figure 7:
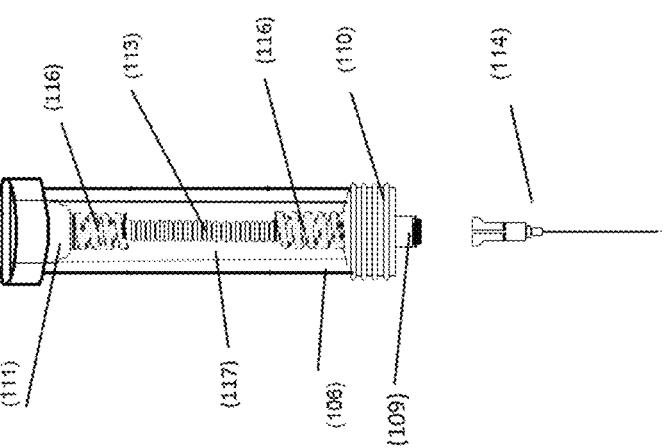
FIG. 7 shows the mechanical system housed inside the piston.
Figure 6:
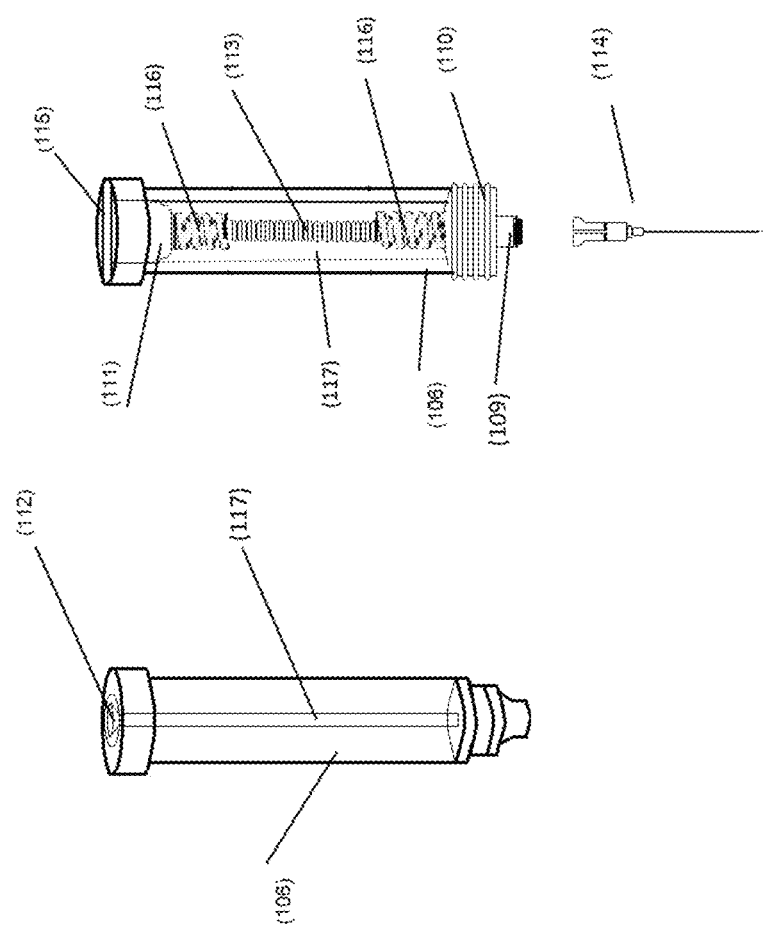
FIG. 6 shows the cavity existing in the piston.

With reference to the figures as shown, the essential elements of the system are immediately evident, formed by a container (101) equipped, in its apical part, with a tooth (102) and two notched fins (104 and 105) which respectively allow the sliding and locking of a piston (106) whose outer surface is therefore characterized by the presence of a "U" shaped system of channels (107) and a double rack 135 system (108-103).

More precisely, inside the container (101) is positioned the tooth (102) which makes the piston slide along the grooved lines (107) therein. The grooved guides (107) sliding along the tooth (102) allow the piston (106) to move first from the bottom upwards to allow the aspiration of the medicinal substances and then, after a rotation, to move from the top bottomwards in order to inject them.

The suction and injection movement of the piston (106) which becomes irreversible thanks to the locking system made possible by the overlapping of the two notched fins (104 and 105) present in the container (101) and the two rack systems (108 and 103) present on the piston (106) which, by interacting with each other, do not allow the piston (106) to go back.

In this way, once the suction action of the medicinal substance in the device has begun, the overlapping of the rack system (103) with the notched fin (105) prevents the return of the piston (106) towards the initial suction position, allowing it to slide in one direction only. Likewise, once the action of injection of the medicinal substance into the device has begun, the overlapping of the rack system (108) with the notched fin (104) prevents the return of the piston to the initial injection position.

The system described above also avoids, in the case of pre-filled retractable needle devices, the accidental release of medicinal substances.

The Piston (106) also has a special cavity (117) at the base of which there is an interlocking housing (109) which hooks and retracts the needle (114) once the injection phase is ended, and from a pad (110) that guides the suction and injection phase of the medicinal substances.

Inside the cavity (117) of the piston (106) a mechanical system is installed consisting, in the upper part by a perforated head (111) which allows the entire system to be fastened inside the piston (106), where the perforated head (111) allows the injection of the medicinal substances into the syringe and has at its upper end a valve (112) which prevents the reflux of the medicament present in the container towards the outside.

The perforated head (111) is connected to an accordion cannula (113), made of any biocompatible material, in turn connected, in the lower part, to the interlocking housing (109) which allows the coupling and therefore the retraction of the needle (114), at the end of the injection.

The perforated head (111) and the interlocking housing (109) are connected to each other by a spring (116), which houses the accordion cannula (113) and commands how this extends and retracts during the operations of inoculation and aspiration of the medicinal substances.

The operator or a special machine, through the accordion cannula (113) existing in the piston (106), after having inserted the latter in the container, can inject the medicinal substance into the container (101) through the perforated head (111), and then close the piston (106) with the protection cap (115).

The present invention has been described in relation to its functionalities for illustrative but not limitative purposes and it is therefore to be understood that variations and/or modifications, also in relation to the shapes, dimensions and measurements of the invention, as well as to the arrangement and materials of the components that compose it can be made without going out of the relative scope of protection.

The invention claimed is:

1. A safety and filling system for retractable needle syringes, characterized by the presence of a barrel (101) provided, in its internal apical part, with a small tooth (102) and two notched fins (104 and 105) as well as a plunger (106) on whose external surface there is the presence of grooved guides in the shape of a "U" (107) and a double rack system (108 and 103) while inside it is equipped with a cavity (117) which, in the upper part it has a perforated head (111) on which a valve (112) is positioned and inside which a mechanical system is installed consisting of an interlocking housing (109) for a needle (114), a spring (116) and an accordion cannula (113).

2. The safety and filling system for retractable needle syringes, according to claim 1, wherein the grooved guides in the shape of a "U" (107) present on the external part of the plunger (106), sliding along the small tooth (102) present in the inner part of the barrel (101) allow the plunger (106) to move first from bottom to top and then from top to bottom.

3. The safety and filling system for retractable needle syringes, according to claim 1, in which, once the suction action of the medicinal substance in the device has begun, the rack system (103 and 108) on the plunger (106) is overlapped on the notched fin (105) present in the barrel (101), thus preventing the return of the plunger (106) towards the initial suction position.

4. The safety and filling system for retractable needle syringes, according to claim 1, in which, once the suction action of the medicinal substance in the device has begun, the rack system (103 and 108) on the plunger (106) is overlapped on the notched fin (104) present in the barrel (101), thus preventing the return of the plunger (106) towards the initial injection position.

5. The safety and filling system for retractable needle syringes, according to claim 1, wherein a mechanical system consisting of a perforated head (111) is installed inside the cavity (117) of the plunger (106), and then closed by a valve (112) surmounted by a stopper (115), in which to inject the medicinal substances, connected to an accordion cannula (113), connected in the lower part to the interlocking housing (109) that allows the coupling and then the retraction of the needle (114) at the end of the injection.

6. The safety and filling system for retractable needle syringes, according to claim 1, in which the accordion cannula (113) is enclosed inside a spring (116), connected to the perforated head (111) and to the interlocking housing (109), which stretches and retracts during the inoculation and aspiration of the medicinal substances.

7. The safety and filling system for retractable needle syringes, according to claim 5, in which the accordion cannula (113) is enclosed inside a spring (116), connected to the perforated head (111) and to the interlocking housing (109), which stretches and retracts during the inoculation and aspiration of the medicinal substances.

* * * * *